United States Patent [19]

Yasuhara et al.

[11] Patent Number: 5,629,461
[45] Date of Patent: May 13, 1997

[54] METHOD OF PRODUCING 1,1,2,2,3-PENTAFLUOROPROPANE

[75] Inventors: Takashi Yasuhara; Akinori Yamamoto; Hirokazu Aoyama; Eiji Seki, all of Settsu, Japan

[73] Assignee: Daikin Industries, Ltd., Osaka, Japan

[21] Appl. No.: 464,833

[22] PCT Filed: Dec. 24, 1993

[86] PCT No.: PCT/JP93/01888

§ 371 Date: Jun. 27, 1995

§ 102(e) Date: Jun. 27, 1995

[87] PCT Pub. No.: WO94/14737

PCT Pub. Date: Jul. 7, 1994

[30] Foreign Application Priority Data

Dec. 29, 1992 [JP] Japan .................... 4-360963

[51] Int. Cl.$^6$ .................... C07C 17/20; C07C 19/08
[52] U.S. Cl. .................... 570/168; 570/166
[58] Field of Search .................... 570/168, 166

[56] References Cited

U.S. PATENT DOCUMENTS

| 3,258,500 | 6/1966 | Swamer et al. | 570/169 |
| 4,147,733 | 4/1979 | Fiske et al. | 570/166 |
| 5,264,639 | 11/1993 | Morikawa et al. | 570/168 |

FOREIGN PATENT DOCUMENTS

| 486333 | 5/1992 | European Pat. Off. | 570/166 |
| 61-238741 | 10/1986 | Japan . | |
| WO90/08753 | 8/1990 | WIPO . | |

*Primary Examiner*—Joseph E. Evans
*Attorney, Agent, or Firm*—Armstrong, Westerman, Hattori, McLeland & Naughton

[57] ABSTRACT

There is provided a method of producing 1,1,2,2,3-pentafluoropropane by reacting 1-chloro-2,2,3,3-tetrafluoropropane with hydrogen fluoride in the presence of fluorinated catalyst. By this method, 1,1,2,2,3-pentafluoropropane can be obtained industrially and economically at high yield.

4 Claims, No Drawings

METHOD OF PRODUCING 1,1,2,2,3-PENTAFLUOROPROPANE

This application is a 371 of PCT/JP/01888 Dec. 24, 1993.

INDUSTRIAL FIELDS WHERE THE INVENTION CAN BE UTILIZED

This invention relates to a method of producing 1,1,2,2,3-pentafluoropropane.

PRIOR ART 1,1,2,2,3-pentafluoropropane (indicated as R-245ca hereafter) is utilized for blowing or cleaning solvent or a heat medium as a substitute for CFC and HCFC. It is especially useful as a urethane blowing agent.

As a method of preparing R-245ca, a process using a chemical reaction by the following formula by Walter et al. is known (J.A.C.S., 77, 4899 (1955)).

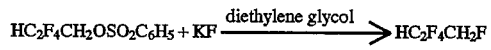

However, this reaction is not suitable for industrial use due to low yield, complicated operation, treatment for KCl after the reaction, generated by use of KF, and high cost.

On the other hand, according to a method described in U.S. Pat. No. 2,980,740, R-245ca is synthesized by reacting 2,2,3,3-tetrafluoropropanol with $SF_4$.

But this method is not suitable for industrial use either, because low yield around 65% is obtained, $SF_4$ is intensely poisonous as strong as phosgene, and the operation is complicated.

As mentioned above, a reaction example for R-245ca suitable for industrial manufacturing is not found at present.

OBJECT OF THE INVENTION

An object of this invention is to provide a manufacturing method suitable for industrial use which enables to produce R-245ca at high selectivity, high yield, good operationability and low cost.

CONSTRUCTION OF THE INVENTION

As a result of repeated eager study by the inventors to aim at an industrial production method for R-245ca by fluorinationg 1-chloro-2,2,3,3tetrafluoropropane (indicated as R-244ca hereafter), they found that R-245ca can be high-selectively produced by reacting R-244ca with hydrogen fluoride in the presence of an appropriate catalyst, having completed this invention.

Catalysts used in the reaction of this invention are fluorinated catalysts, for example, there can be used metal fluorides and/or metal oxyfluorides produced by fluorinating metal oxid, with HF separated from solution of metal salt by use of alkali or the like.

In this case, hydrochloride and nitrate can be used as the metal salt. And, ammonia, carbamide, and metal hydroxide can be used as the alkali.

Besides, for a method of obtaining chromium oxide, a method of obtaining it by reducing $CrO_3$ can be adopted, and for a method of obtaining the chromium oxyfluoride, a method of treating $CrF_3(nH_2O)$ with oxygen etc. under heating can be adopted.

For the metals used, one kind of or a mixture of two or more kinds of metals selected from alminium, chromium, manganese, nickel and cobalt can be used.

Those metal fluorides can be supplied by themselves, as well as carried on suitable carriers. For the carriers, active carbon, fluorinated alminium and so on can be used.

A reaction temperature can be adequately chosen from the range of 250° to 450° C., but too lower temperature is not practical due to slow reaction. The reaction temperature is desirable to be from 300° to 400° C.

The excess ratio of HF to R-244ca can be selected adequately from the range of 1 to 100 according to the objective conversion rate, the rate of the product, the contact times and the reaction temperature. That is, HF to R-244ca may be from 1:1 to 100:1. However, although the reaction can be carried out even if the excess ratio of HF is over 100, the productivity decreases not to be practical.

The yield of the target product can be raised by refluorinating the raw material returned to a reactor after separating necessary components from the reaction product.

R-244ca used in this invention can be obtained by reacting $CF_2HCF_2CH_2OH$ (2,2,3,3-tetrafluoropropane-1-ol) with thionyl chloride.

POSSIBILITY OF UTILIZING THE INVENTION IN INDUSTRY

The production method of this invention is suitable for the industrial use, because the economical HF is used, R-244ca can be continuously fluorinated by gaseous phase reaction, and the selectivity and yield of the product can be improved.

EMBODIMENTS

The invention will be explained in the following examples which can be variously modified on the basis of the technical concept of this invention.

Preparation Example 1

Chromium hydroxide prepared from aqueous chromium nitrate and aqueous ammonia was separated by filtering, washed with water, dried at 100° C., then molded into cylindrical shape having diameter of 3 mm and hight of 3 mm by a tapping-type molding machine.

Thus obtained catalyst was filled in a Hastelloy C-made reaction tube and heated to be kept at 400° C. for 1 hour under nitrogen flow. Then, the temperature was lowered to 200° C. and hydrofluoric anhydride was supplied to treat the catalyst for 1 hour to activate.

Operation Example 1

10 cc of the catalyst obtained in Preparaiton example 1 was filled in a reaction tube and the reaction temperature was controlled at 350° C., and then 200 cc of HF and 35 cc of R-244ca were introduced in gaseous state.

R-244ca used here was prepared by the following steps:

20 cc of active carbon was filled in a Hastelloy C-made reaction tube and treated at 300° C. for 2 hours under nitrogen flow. Then the temperature was lowered to 200° C., $HCF_2CF_2CH_2OH$ and $SOCl_2$ were introduced into the reaction tube respectively at 26.4 g/hr and 24 g/hr as supply rate. The product was removed at a water-washing column and then recovered in a cold trap cooled with water. R-244ca was obtained by rectification and separation of the recovered organic compound.

The product was washed with water and then analyzed by gas-liquid chromatography (GLC). The result is shown in the following table-1.

In this table-1, 2,3,3-trifluoro-1-propene is indicated as R-1243, 1,2,3,3-tetrafluoro-1-propene as R-1234 and 1-chloro-2,3,3-trifluoropropene as R-1233.

The condition of GLC analysis: PORAPACK-Q 3 m. Under temperature elevated at 10° C./min from 100° C.

TABLE 1

| | |
|---|---|
| R-1243 | 2.6% |
| R-1234 | 0.8% |
| R-245ca | 66.2% |
| R-1233 | 0.5% |
| R-244ca | 29.9% |

According to this result, it is understood that the reaction based on this invention can bring about easy production of the objective R-245ca at high selectivity and is suitable for the industrial use.

Preparation Example 2

A catalyst was prepared under the same condition as that of Preparation example 1 except changing chromium nitrate used in Preparation example 1 to a mixture of alminium nitrate and chromium nitrate (1:1 of mole ratio).

Operation Example 2

A reaction was carried out under the same condition as that of Operation example 1 except using the catalyst obtained in Preparation example 2. The result of GLC analysis is shown in the following table-2.

TABLE 2

| | |
|---|---|
| R-1243 | 2.4% |
| R-1234 | 0.7% |
| R-245ca | 35.2% |
| R-1233 | 0.5% |
| R-244ca | 61.2% |

This result also shows that in the reaction according to this invention the target product can be obtained at good selectivity.

What is claimed is:

1. A method of producing 1,1,2,2,3-pentafluoropropane which comprises: reacting 2,2,3,3-tetrafluoropropanol with thionyl chloride to obtain 1-chloro-2,2,3,3-tetrafluoropropane; and then reacting the 1-chloro-2,2,3,3-tetrafluoropropane with hydrogen fluoride in the presence of a fluorinated catalyst.

2. A method according to claim 1, wherein the fluorinated catalyst is a fluoride or oxyfluoride obtained by fluorinating at least one oxide selected from the group consisting of oxides of aluminum, chromium, manganese, nickel and cobalt, with hydrogen fluoride.

3. A method according to either claim 1 or 2, wherein the 1-chloro-2,2,3,3-tetrafluoropropane is reacted with hydrogen fluoride at a temperature in the range of from 250° to 450° C.

4. A method according to claim 3, wherein 1 to 100 moles of hydrogen fluoride are reacted with one mole of 1-chloro-2,2,3,3-tetrafluoropropane.

* * * * *